(12) United States Patent
Holbeche et al.

(10) Patent No.: US 9,295,535 B2
(45) Date of Patent: Mar. 29, 2016

(54) DEVICE FOR GENERATING GASEOUS SPECIES

(71) Applicants: Thomas Bickford Holbeche, Church Crookham (GB); Cormac John Devery, Felbridge (GB); Geoffrey Morgan Lloyd, College Town (GB)

(72) Inventors: Thomas Bickford Holbeche, Church Crookham (GB); Cormac John Devery, Felbridge (GB); Geoffrey Morgan Lloyd, College Town (GB)

(73) Assignee: Linde Aktiengesellschaft, Munich (DE)

( * ) Notice: Subject to any disclaimer, the term of this patent is extended or adjusted under 35 U.S.C. 154(b) by 0 days.

(21) Appl. No.: 14/265,463

(22) Filed: Apr. 30, 2014

(65) Prior Publication Data
US 2014/0234795 A1 Aug. 21, 2014

Related U.S. Application Data

(63) Continuation of application No. 13/254,874, filed as application No. PCT/GB2010/000413 on Mar. 9, 2010, now abandoned.

(30) Foreign Application Priority Data

Mar. 11, 2009 (GB) .................................. 0904198.9
Mar. 12, 2009 (GB) .................................. 0904221.9

(51) Int. Cl.
| | | |
|---|---|---|
| A61C 17/16 | (2006.01) | |
| A61C 17/02 | (2006.01) | |
| H05H 1/24 | (2006.01) | |
| A61C 19/06 | (2006.01) | |
| A46B 15/00 | (2006.01) | |
| A46B 11/00 | (2006.01) | |

(52) U.S. Cl.
CPC ......... *A61C 17/0202* (2013.01); *A46B 11/0017* (2013.01); *A46B 15/0024* (2013.01); *A61C 19/066* (2013.01); *H05H 1/2406* (2013.01); *A46B 2200/1066* (2013.01); *H05H 2240/10* (2013.01); *H05H 2240/20* (2013.01)

(58) Field of Classification Search
CPC .... A61C 17/02; A61C 19/066; H05H 1/2406; H05H 2240/10; H05H 2240/20; A46B 15/0024; A46B 11/0017; A46B 2200/1066
See application file for complete search history.

(56) References Cited

U.S. PATENT DOCUMENTS

| | | | | |
|---|---|---|---|---|
| 6,455,014 B1 * | 9/2002 | Hammerstrom et al. | 422/186.04 |
| 6,465,964 B1 * | 10/2002 | Taguchi et al. | ........... 315/111.21 |
| 8,203,096 B2 * | 6/2012 | Sanders et al. | ........... 219/121.48 |
| 2002/0187066 A1 * | 12/2002 | Yu et al. | .......................... 422/22 |
| 2011/0183284 A1 * | 7/2011 | Yamanaka et al. | .............. 433/32 |

* cited by examiner

Primary Examiner — Kishor Mayekar
(74) Attorney, Agent, or Firm — David A. Hey

(57) ABSTRACT

The present invention provides a device for generating a non-thermal gas species which may be a flow of gas plasma in the form of a gas plasma plume emitted from the device. The device comprises a gas capsule, or pressure vessel for holding a gas or gases under pressure and forming a flow of gas through a reaction generator to an applicator when released from the capsule. Gas released from the gas capsule is energised in the reaction generator to form the gas plasma. The device is designed to be hand held and hand operated so that it may be used for cleaning and whitening teeth as well as other applications.

17 Claims, 11 Drawing Sheets

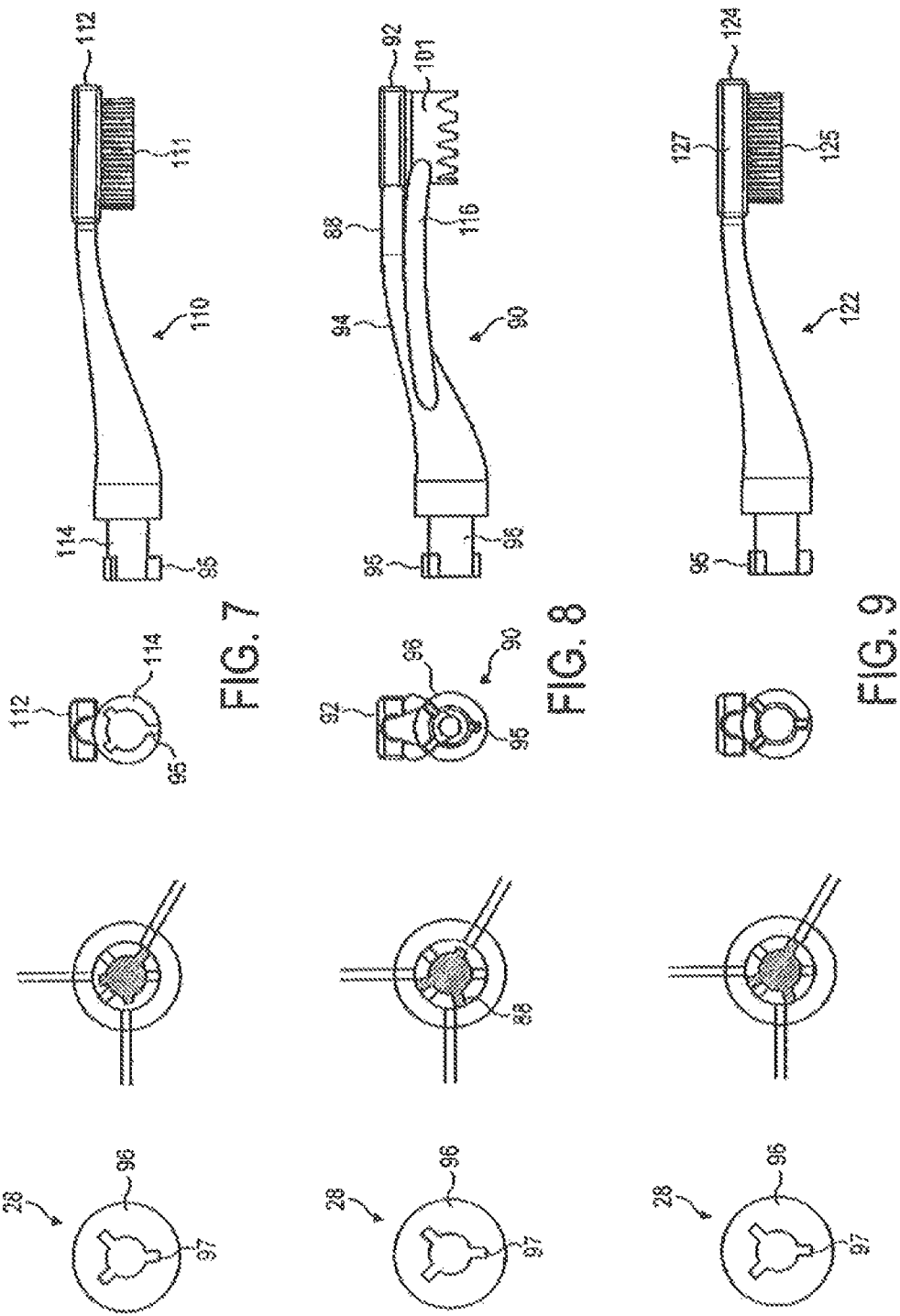

DEVICE FOR GENERATING GASEOUS SPECIES

This application is a continuation application of U.S. patent application Ser. No. 13/254,874 filed 5 Oct. 2011, which is a US National Phase application of international patent application PCT/GB2010/000413 filed 9 Mar. 2010, which claims priority to Great Britain patent application 0904221.9 filed 12 Mar. 2009 and to Great Britain patent application 0904198.8 filed 11 Mar. 2009.

The present invention relates to a device for generating gaseous species such as a non-thermal gas plasma and to an apparatus comprising the device and a recharging unit.

Systems for generation of non-thermal gas plasma (also referred to as "non-equilibrium" gas plasma) are known hereto and have utility in a number of fields such as industrial, dental, medical, cosmetic and veterinary fields for the treatment of the human or animal body. Non-thermal gas plasma generation can be employed to promote coagulation of blood, cleaning, sterilisation, and removing of contaminants from a surface, disinfection, re-connection of tissue, and treatment of tissue disorders without causing significant thermal tissue damage. The plasma itself may be applied to a surface to be treated or may act as a precursor to a reactive or modified gaseous species that is applied to the surface.

Known gas plasma generators are generally either industrial systems of considerable size for processing or functionalizing relatively large substrates or smaller systems comprising a base unit having a heavy duty gas cylinder connected by a gas line to a hand-piece. Additionally, the system may comprise a power unit connected by a power cable to the hand piece. These systems are not therefore well suited to domestic or in-surgery use.

The present invention provides a device for generating a flow of a non-thermal gaseous species, comprising: a gas capsule for holding a gas under pressure and forming a flow of gas to a reaction generator when released from the capsule; a reaction generator in which gas released from the capsule can be energised to generate the gaseous species; a source of electrical energy; energising means electrically connected to the source of electrical energy for energising gas in the reaction generator to form the gaseous species; and a housing for housing the gas capsule, reaction generator, source of electrical energy, and energising means, wherein the device has a size and weight such that the device can be held and operated by a user by hand and the flow of gaseous species directed to treat a treatment region of an object or human or animal body.

The species generated may be a non-thermal plasma, at a temperature less than 40° C. In this case, the energising means are adapted to generate plasma in a plasma generator.

A control may be provided for selectively releasing gas from the gas capsule for forming the flow of gas. The control may additionally be operably connected to the energising means for controlling energisation of the electrodes. A sensor may be provided for sensing the flow of gas released from the gas capsule and wherein the control allows activation of the energising means only if the flow of gas is above a predetermined mass or volume flow rate. The control may comprise a user input means, such as a manually operable button or switch, operable by a user for causing flow of gas to the reaction generator and activation of the energising means.

The housing may comprise means for locating a the gas capsule in the housing so that the gas capsule is operable to release gas for forming the gas flow and wherein the locating means is adapted such that a the gas capsule can be removed from the housing so that a replacement the gas capsule can be located in the housing by the locating means. A gas release mechanism may be operable for releasing gas from the gas capsule when the locating means locates a the gas capsule in the housing. The gas capsule may comprise a pressure release valve, such as a Schrader valve, biased to prevent the release of gas from the gas capsule and the gas release mechanism comprises means for operating on the pressure release valve against the bias for releasing gas from the gas capsule.

The housing may comprise a conduit extending between the gas capsule and the reaction generator for directing the flow of gas released from the gas capsule. A flow valve which when open may allow the flow of gas through the conduit from the gas capsule to the reaction generator, and when closed may resist the flow. Alternatively or additionally, a flow regulator may be provided for regulating the flow of gas between the gas capsule and the reaction generator and/or the flow of species from the reaction generator to an applicator. In this way, the flow of gas entering the entering the reaction chamber can be controlled to allow reaction to occur and the flow of species ejected from the device can be controlled to allow treatment to occur.

An expansion chamber may be provided in which gas can be released from the gas capsule for controlled release through an orifice plate. The expansion chamber reduces flow speed from the gas capsule.

The gas capsule contains a sufficient amount of gas prior to use for generating a species to treat a treatment region of an object or human or animal body for a time sufficient to achieve a beneficial effect on the treatment region. In this regard, the gas capsule may contain a sufficient amount of gas for generating a plasma for at least two minutes. The generation of species sufficient to provide a beneficial effect on a treatment region (such as the teeth in an oral cavity) requires generally half a liter of gas per minute at atmospheric pressure. Accordingly, the gas capsule may contain the equivalent of up to four liters of gas at atmospheric pressure stored at a pressure of at least 60 bar. The internal volume of the gas capsule may be in the range of 10 ml to 100 ml. The gas capsule may be generally cylindrical and less than approximately 100 mm in length and 35 mm in diameter.

The energising means may comprise at least one electrode for generating an electric field in the reaction generator and a signal generator for generating an electrical signal for driving the at least one electrode. If the species generated is a gas plasma, the energising means may be configured to generate a non-thermal plasma at a temperature which is preferably less than about 40° C. which is tolerable by a user. At least one of the electrodes may be insulated from gas in the plasma generator by a dielectric to reduce arcing and thereby limit heating of the species. The at least two electrodes may be spaced apart one from another in order to generate an electric field in substantially all of the plasma generator. One of the electrodes may be formed around a periphery of the plasma generator. One of the electrodes may be formed by a probe extending into the plasma generator. The probe may be tapered at an end portion thereof to form a point for increasing the generation of plasma in the plasma generator.

The signal generator may be configured to generate an RF, AC or pulsed DC signal for driving the electrodes which may be at a low duty cycle signal in which the energy is provided to the or each of the electrodes for less than 10% of the cycle, If the species is a gas plasma, its generation may be initiated in the reaction generator and continue without requiring continuous energisation by the energising means. The signal generator may generate an RF signal greater than 20 kHz so that the signal generator is not audible to a user.

The energising means may comprise an amplifier for amplifying the signal for driving the electrodes and a matching circuit for matching impedance of the load and the source.

The source of electrical energy may be one or more batteries. The batteries are preferably rechargeable and the housing comprises a socket for receiving a plug connected to a mains power source and a recharging circuit for recharging the batteries. Alternatively, the device may comprise means for inductively coupling the batteries to a recharging unit for recharging. The housing may comprise an enclosure for locating the batteries in the housing and electrical terminals which connect to the batteries when located in the enclosure for supplying energy to the energising means.

Alternatively, the source of electrical energy may comprise a transformer and the housing comprises means for connection to an electrical power supply and wherein the transformer is adapted to supply energy to the energising means. Typically, depending on its configuration, a plasma generator requires a high voltage to be stuck in order to initiate a non-thermal gaseous plasma. One or more step-up transformers may convert a DC voltage from a battery to a plasma-initiating voltage.

An applicator may be provided for conveying species from the reaction chamber and applying species to a treatment region. A gaseous plasma requires the passage of an electrical current through it to maintain it in being. Once the gas is removed from the plasma generator, ionic species tend to recombine with free electrodes and excited species return to their ground states. A gas so removed from a plasma generator is sometimes referred to as an "afterglow". These changes typically take place in the applicator. The applicator may comprise an applicator head for applying species and a duct for ducting species from the reaction chamber to the head. The applicator head may be spaced from the reaction generator thereby reducing contamination of the plasma generator and/or separating the treatment region from the energising means, which may be high voltage.

The device has many applications but may be adapted to treat an oral region of a human or animal body by whitening or cleaning teeth. In this regard, the applicator head may be sized and shaped to fit over one or more teeth. The applicator head may comprise one or more channels configured to be located in the mouth of a human or animal body for directing species for treating a plurality of teeth.

Evacuation means may be provided for evacuating species from the treatment region after treatment and may comprise pumping means driven by a motor for pumping species from the treatment region. An exhaust duct may extend from the treatment region and be in fluid communication with the pumping means. The exhaust duct may be formed by the applicator. The control may additionally control operation of the evacuation means together with the supply of gas to the reaction chamber and activation of the energising means. The evacuation means causes a flow of gas or species from the treatment region which is preferably greater than the flow of gas to the treatment region caused by release from the gas capsule.

A display may be provided for displaying a value representative of a condition of the device which can be one or more of: the gas content of the capsule, the amount of charge remaining in the source of electrical energy, or a temperature of the plasma emitted from the device. Means may be provided for alerting a user, such as a sound which is audible to user or a warning light, when a condition of the device decreases below a predetermined amount.

The gas capsule may contain a gas having low energy requirement for forming a non-thermal plasma in the reaction chamber. In this way, the amount of energy injected into the reaction chamber can be reduced thereby avoiding excessive heating of the gas or species. The gas may be a noble gas such as helium when a non-thermal plasma is to be generated. The gas capsule may contain oxygen and the gaseous species generated when the gas is energised is ozone.

In order to permit the device to be used by hand, it is preferable that it is less than 300 mm in length and 50 mm in breadth and has a mass of less than 1 kg.

The present invention also provides apparatus comprising the device and a recharging unit comprising: a recharging gas pressure vessel containing gas for supplying gas to the gas capsule of the device; and/or electrical recharging means for recharging the source of electrical energy in the device. Alternatively, the device may employ disposable gas batteries and a disposable gas capsule. A further alternative is for the gas capsule to be rechargeable, but this operation to be performed remote from the device.

The recharging unit and gas capsule of the device may comprise respective recharging valves which can be opened when the device and unit are connected to allow the supply of gas to the gas capsule and are closed when not connected.

The recharging unit may comprise a seat for seating the device, and wherein when the device is seated in the recharging unit the gas capsule and the recharging pressure vessel are connected to allow the supply of gas to the gas capsule. A conduit may be provided having a first end portion adapted for engaging with and opening the recharging valve of the gas capsule and a second end portion for engaging with and opening a recharging valve of the device pressure vessel. Alternatively, the recharging apparatus may comprise a seat for seating the gas capsule when it has been removed from the device and wherein when the gas capsule is seated in the recharging unit the pressure vessels are connected to allow the supply of gas to the gas capsule. In this arrangement, at least two gas capsules may be provided, such that at any one time one capsule can be seated in the recharging unit for recharging and one capsule can be housed in the device housing for use in generating a non-thermal species.

The electrical recharging means may comprise a recharging circuit for receiving electrical energy from a supply and supplying the electrical energy for recharging the source of electrical energy in the device when the source of energy is connected to the electrical recharging means. The recharging unit may comprise a seat for seating the device, and wherein when the device is seated in the recharging unit the source of energy is connected to the electrical recharging means for recharging the source of electrical energy.

Alternatively, the recharging unit may comprise a seat for seating the source of electrical energy when the source has been removed from the device and wherein when the source is seated in the recharging unit the source of energy is connected to the electrical recharging means for recharging the source of electrical energy.

In order that the present invention may be well understood, embodiments thereof, which are given by way of example only, will now be described with reference to the accompanying drawings, in which:

FIG. 7 shows a first applicator of the device and a connecting portion of the device housing;

FIG. 8 shows a second applicator of the device and the connecting portion of the device housing;

FIG. 9 shows a third applicator of the device and the connecting portion of the device housing;

Figure 1:
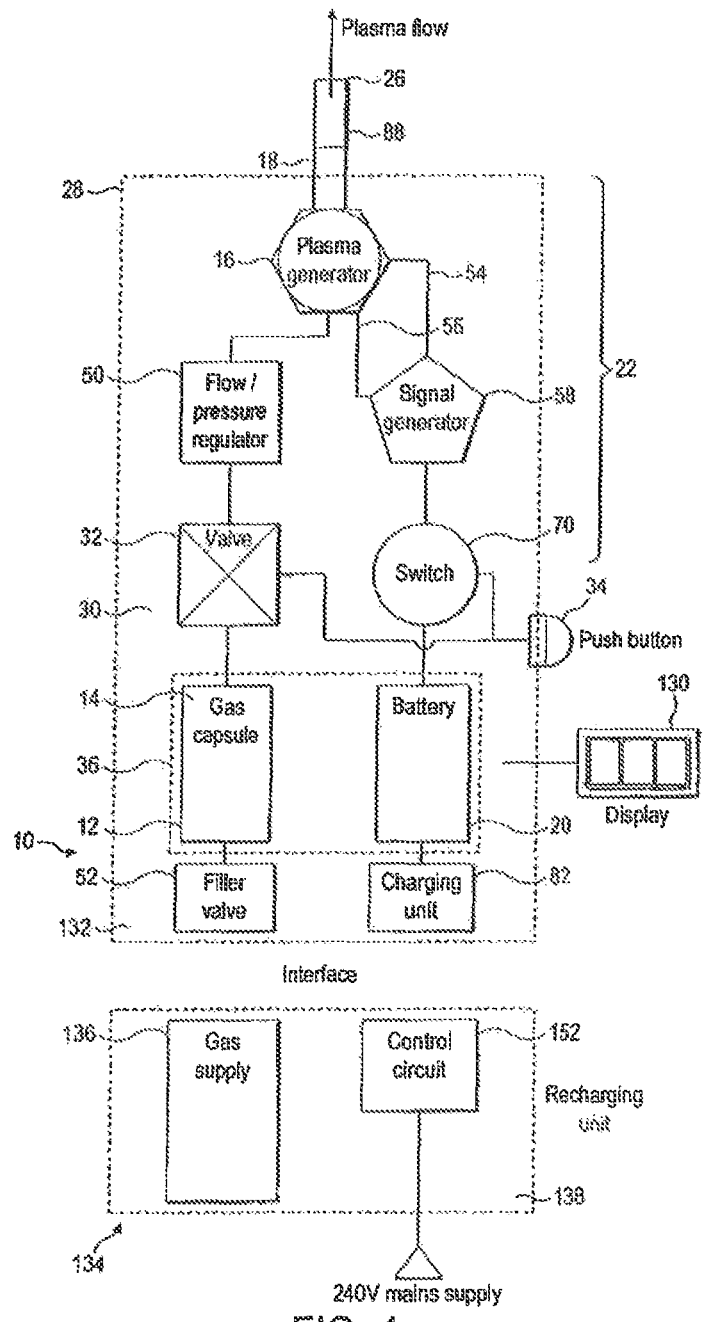
FIG. 1 shows schematically apparatus comprising a device for generating a non-thermal plasma and a recharging unit.
Figure 2:
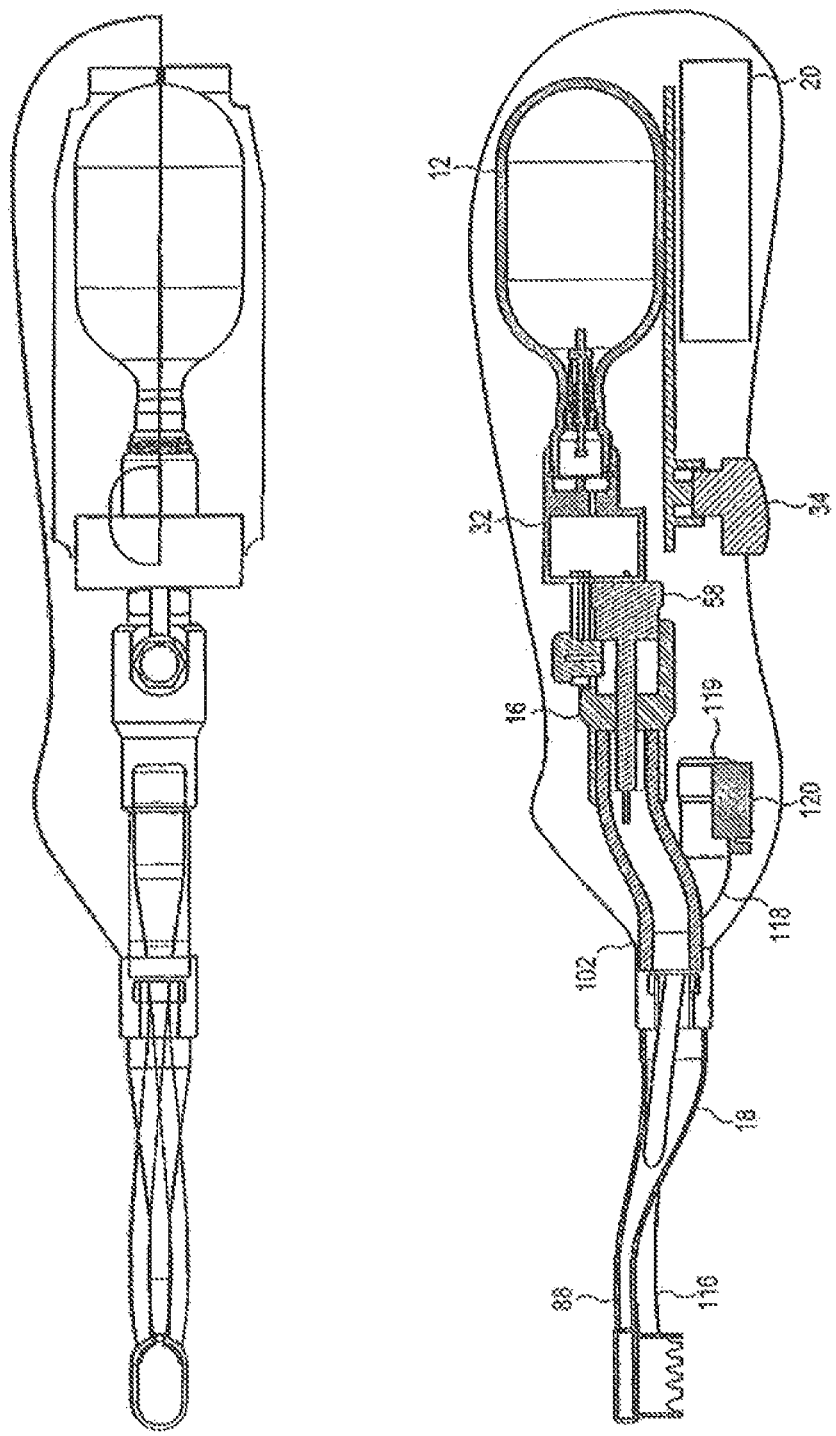
FIG. 2 shows a perspective cut-away view of the device.

Referring to FIGS. 1 and 2, a device 10 is shown for generating a non-thermal plasma 24 which may be a flow of gas plasma in the form of a gas plasma plume emitted from the device. The flow of gas plasma is generated and emitted from the device generally at atmospheric pressure. The device comprises a gas capsule, or pressure vessel, 12 for holding a gas or gases 14 under pressure and forming a flow of gas through a plasma generator 16 to an applicator 18 when released from the capsule. Gas released from the gas capsule is energised in the plasma generator to form a gas plasma.

Figure 1A:
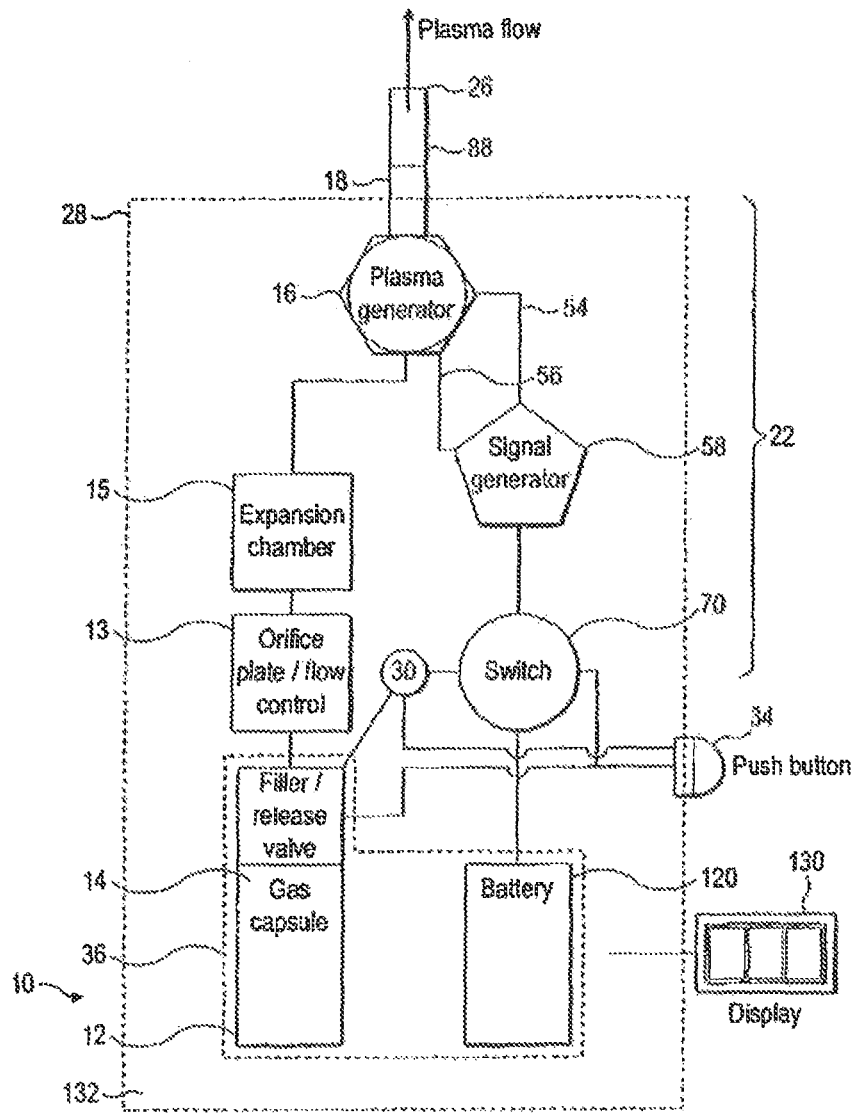
FIG. 1a shows a modified device.

In a modified device shown in FIG. 1a, high pressure gas may flow from the capsule through an orifice plate 13 into an expansion chamber 15 which slows flow and which can then be released in a controlled way to the reaction generator 16.

The device further comprises a source of electrical energy 20 and gas plasma energising means 22 electrically connected to the source of electrical energy for energising gas 14 in the plasma generator 16 to form a gas plasma 24. The applicator 18 directs flow of plasma from the plasma generator 16 for generating a gas plasma plume from an opening 26 in the applicator. Gas plasma may be mixed with ambient air in a suitably configured applicator.

A housing 28 houses the gas capsule 12, plasma generator 16, source of electrical energy 20, and plasma energising means 22. The device is sized and of a weight such it can be held and operated by a user by hand and the plasma 24 readily directed by a user to treat a treatment region of an object or human or animal body. In this regard, the device is operable without the requirement for its connection by a gas line to a gas supply. Such a prior art arrangement is cumbersome and does allow the device to be portable. The self-contained arrangement of the device 10 allows easy use in a domestic environment, for instance, in a bathroom. The device 10 may receive power from the source without the requirement for electrical cabling connecting the device to a mains supply. However, typically electrical cabling is less of an impediment to use in the domestic environment than a gas line, as cabling is usually flexible and light-weight, although in device 10 electrical cabling is not required when the device is in use.

In order that the device is suitable to be held and operated by hand, it should not exceed an upper size or an upper weight. It will also be appreciated that treatment of a treatment region using the device may require intricate and fine movements which are possible if the device is hand-held only if it is relatively light. In one example, the device is approximately the size and mass of a typical electric tooth brush. Other known hand-held and operated devices in other fields, which are provided herein to aid understanding of the size and mass of the device 10, are for example an electric tooth brush, or cordless electric drill or screw driver. Accordingly, the upper size of housing 28, or the device as a whole, is approximately 30 cm in length by 5 cm in breadth. The upper limit of the breadth is determined by the ability of a hand to hold the device. Any size of housing significantly above 50 mm diameter renders the device uncomfortable to hold and use. The upper of the length is determined by the ability of a user to use the device without it becoming unwieldy and it will also be appreciated that if the device is used to treat teeth, the device must be less than an arm's length and preferably in the region of about 20 cm. Preferably, the housing 28 is contoured to so that it can be held comfortably in the palm of the hand. The mass of the housing, or device as a whole, is preferably less than one kilogram.

The device may be configured for use in a single treatment and then be disposable. In this regard, the components of the device are selected for only a single treatment. As a single treatment may require less gas and less energy stored in the device, the pressure vessel and source of energy can be selected to minimize manufacturing costs and reduce the size and weight of the device. For example, the device may be configured to treat an oral cavity only once and then be disposable. Such a disposable device may be more easily portable for instance in a jacket pocket or hand-bag. As the device is suitable for dry cleaning teeth or other treatment, a disposable device can readily be used whilst travelling for example since water is not always available for performing a treatment.

The device 10 may be used for example in the dental, medical, cosmetic and veterinary fields for the treatment of the human or animal body. The device has particular utility in dental or other oral treatments, for example, teeth whitening or dry cleaning of teeth, sterilization after root canal treatment, wound sterilization or healing (for example dry pockets after extractions). The application for teeth whitening is described in more detail in the applicant's co-pending application number GB 0823435.3 filed 23 Dec. 2008, the contents of which are hereby incorporated by reference. In this regard, the treatment region may be a single tooth, two teeth or the upper and/or lower arch of teeth. Alternatively, the treatment region may be a portion of the gingiva or a pocket. Still further, the treatment region may be the oral cavity.

The device 10 may also be used in non-medical applications such as the treatment of surfaces by plasma processing, for example, the preparation of a plastics surface prior to the application of a paint.

The components of device 10 will now be described in more detail, giving modifications and alternatives where relevant.

A control indicated generally at 30 is provided for selectively releasing gas from the gas capsule for forming the flow of gas. As shown in this example, the control comprises a valve 32 which when open allows the flow of gas through a conduit from the gas capsule to the plasma chamber, and when closed resists flow. The control 30 comprises a mechanical push switch 34 which can be operated by a user for controlling the valve 32. Alternatively, other user activation means can be provided to operate the valve, such as a mechanical slide switch or an electronic switch which can be closed for example to open a solenoid valve. Still further, the user activation means may be adapted such that flow can be activated from the gas capsule in response to first user input and deactivated in response to a second user input. Alternatively, a single user input may activate a timer circuit (not shown) to allow gas flow for a predetermined period of time sufficient to treat a treatment region. For example if the device 10 is used for teeth whitening the predetermined period may be 5 seconds for each tooth.

The valve 32 may be any suitable means for opening and closing flow between the gas capsule and the plasma generator. Further, the valve may be variable for adjusting the flow between fully open and fully closed, for example a butterfly valve.

The housing 28 comprises means 36 for locating the gas capsule 12 in the housing so that the gas capsule is operable to release gas for forming the gas flow. The locating means 36 may be adapted such that the gas capsule 12 can be removed from the housing for example when the gas contained therein is depleted or low so that a replacement gas capsule which is full can be located in the housing. In this regard, the locating means may comprise a chamber shaped for receiving the gas capsule and a closure member (not shown) for closing the chamber when the gas capsule is located in the chamber. In another example, the gas capsule may be push-fitted or screw-fitted into the chamber.

The housing may comprise a formation or other gas release mechanism operable for releasing gas from the gas capsule when the locating means locates the gas capsule in the chamber. The gas capsule may comprise a pressure release valve biased to prevent the release of gas from the pressure vessel. The gas release mechanism operates on the pressure release valve against the bias for releasing gas from the capsule.

Figure 3:
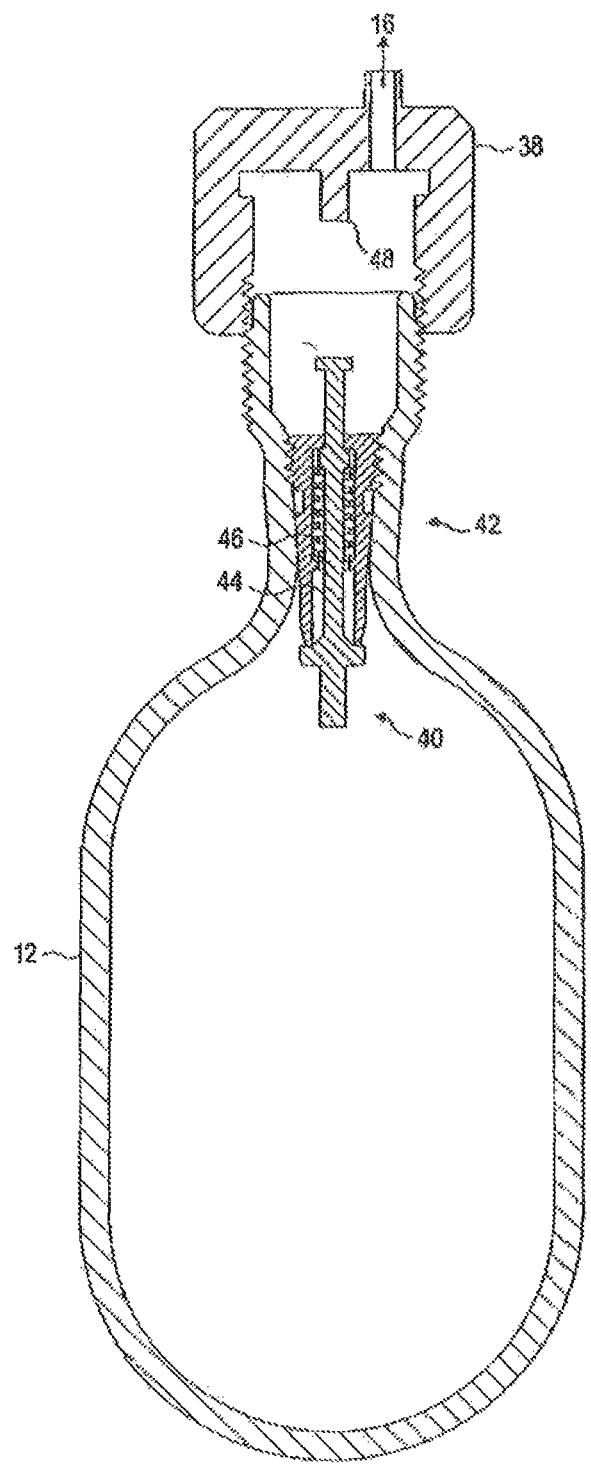
FIG. 3 shows a cut-away view of a pressure vessel of the device.

One example of the gas release mechanism and pressure release valve is shown in FIG. 3. The housing comprises a conduit 38 extending between the gas capsule 12 and the plasma generator 16 for directing the flow of gas released from the gas capsule. The gas capsule 12 comprises a valve 40 at the head 42 of the capsule. In this example locating means comprises an outer surface of the head 42 which is threaded for engaging with a complimentary threaded surface of the housing for locating the pressure vessel in position. The valve 40 comprises a sliding member 44 received for sliding movement in the neck of the pressure vessel and biased by a biasing means, which in this example is a spring 46, into a closed position. When the pressure vessel is located in the housing, a formation, or protrusion, 48 engages the sliding member 44 pushing it into the vessel (as shown by arrows in FIG. 3) and opening the valve to allow gas flow from the vessel. The valve 40 has sufficient sealing strength to retain gas in the pressure vessel at the maximum pressure of the vessel, for example, 80 bar. The valve may be a Schrader valve.

Alternative sealing or valve arrangements for the capsule are possible. For example, the mouth of the capsule may be closed fluid-tight by a seal. Delivery of gas may be effected by piercing the seal with a hollow needle which is open at both ends. The proximal end of the needle may communicate with a conduit having a pressure regulator disposed therein, so as to regulate the gas flow to the plasma cell.

Although a separate valve 32 is shown in FIG. 1 for selectively allowing flow of gas to the plasma generator 16 in addition to the pressure release valve 40, in an alternative arrangement, the valve 32 can be omitted such that control of gas flow is controlled solely by the pressure release valve optionally into an expansion chamber 11 and released in a controlled fashion via an orifice plate.

The mass or volume flow rate of gas entering the plasma chamber 16 is preferably controlled to promote the generation of a non-thermal or non-equilibrium gaseous plasma. For instance, the rate of flow controls the residence time of gas in the plasma chamber. If the rate is too high, gas may flow through the plasma chamber without being energised to form a gas plasma. Additionally, even if plasma is formed, the flow through the applicator may be more than is required to achieve a beneficial result of the treatment region and therefore wasteful of gas. If the rate of flow is too slow, insufficient plasma flow is generated through applicator resulting in inadequate treatment of the treatment region or generation of an undesirable or non-therapeutic gaseous species. Accordingly, the device 10 comprises a flow regulator 50 for regulating the flow of gas between the gas capsule and the plasma generator. Additionally or alternatively, a flow regulator can be located to regulate the flow of gas and plasma from the plasma generator. The flow regulator may be a variable flow control valve arranged in a feed back loop with a flow sensor 72 (see FIG. 4). As an alternative to a flow regulator, a pressure regulator may be provided for regulating the pressure of gas in the plasma generator. Preferably, the flow regulator is operable to achieve constant flow of gas to the plasma generator throughout a pressure range of gas in the gas capsule that is, relatively high pressure when the capsule is full and relatively low pressure when the capsule becomes empty.

The required amount of exposure of a treatment region to plasma (or other gas species generated by the plasma) varies depending on the type of treatment which the device 10 is adapted to perform. Accordingly, the gas capsule contains a sufficient amount of gas prior to use for generating a plasma to treat a treatment region of an object or human or animal body for a time which is sufficient to achieve a beneficial, or therapeutic, effect on the treatment region. For example, if it takes 5 seconds to whiten a single tooth at a flow rate of one liter per minute, and a typical mouth contains 32 teeth, the gas capsule should contain at least 2.66 liters of gas at atmospheric pressure. Preferably, the gas capsule contains sufficient gas and operates at lower flow rates for a plurality of treatments.

The gas capsule may contain a sufficient amount of gas for generating a (plasma) plume for at least two minutes or the generation of a (plasma) plume sufficient to provide a beneficial effect on a treatment region. Once the plasma leaves the confines of the plasma generator 16 and passes into the applicator 18, it no longer, strictly speaking, remains a plasma but becomes an afterglow which contains decay ionic and excited gaseous species. When the afterglow leaves the applicator 18 it becomes a plume. Air gases are induced into the plume and these air gases may react with subsisting free radicals, excited species or charged species in the plume to form reactive oxygen and/or reactive nitrogen species which may take part in useful chemical reactors at a substrate, for example, in chemical reactions that act to destroy oral bacteria or whiten teeth in vivo or remove stains therefrom.

The amount of gas which can be contained in the pressure vessel, or gas capsule, is limited by the design of the pressure vessel and overall weight and size of the device. In this latter regard, a relatively heavy pressure vessel may be capable of storing large quantities of gas, however, such a heavy vessel is not suitable for the device 10 as it would render the device incapable of being held and operated by hand. It has been found that a suitable gas capsule is adapted to contain the equivalent of approximately four liters of gas at atmospheric pressure stored at a pressure of at least 80 bar and typically up to a value in the range of 200 to 300 bar. The gas capsule may have an internal volume sufficient to contain between 10 ml to 100 ml of water. The gas capsule may be generally cylindrical and less than 100 mm in length and 35 mm in diameter. In the example shown in FIG. 2, the gas capsule is approximately 100 mm in length and 35 mm in diameter. The vessel may be made from aluminium or stainless steel, or mild steel or any other suitable robust material.

As shown in FIG. 1 and described in more detail below, the device 10 comprises a filler valve 52 for allowing gas from a gas supply to re-fill or recharge the gas capsule 12. The filler valve 52 is in normal use, closed to prevent evacuation of gas from the gas capsule and can be opened when it is desired to recharge the vessel. The valve 52 may be similar to the arrangement shown in FIG. 3 in that a recharging unit engages with the valve 52 to open the valve and allow the recharging of gas. Additionally, the gas capsule may be formed integrally and form part of the housing 28 and re-filled when empty. Alternatively the gas capsule 12 can be withdrawn from the device 10 and inserted into the recharging unit 134 by the user.

The plasma energising means 22 comprises two electrodes 54, 56 for generating an electric field in the plasma generator 16. In certain configurations a single electrode may be provided and more than two electrodes may be provided for example with two electrodes receiving a driving signal and one electrode being earthed, A signal generator 58 generates an electrical signal for driving, or energising, the electrodes. At least one, and preferably both or all, of the electrodes are dielectric barrier discharge electrodes insulated from gas in the plasma chamber by a dielectric to prevent excessive heating of the plasma caused by continuous or prolonged arcing. Suitable dielectric materials are ceramic, plastics or glass. Insulating the or each electrode reduces the duration of arcing in the plasma chamber when an electric current flows from one electrode through the plasma or gas to the other electrode or each of the other electrodes.

Figure 4:
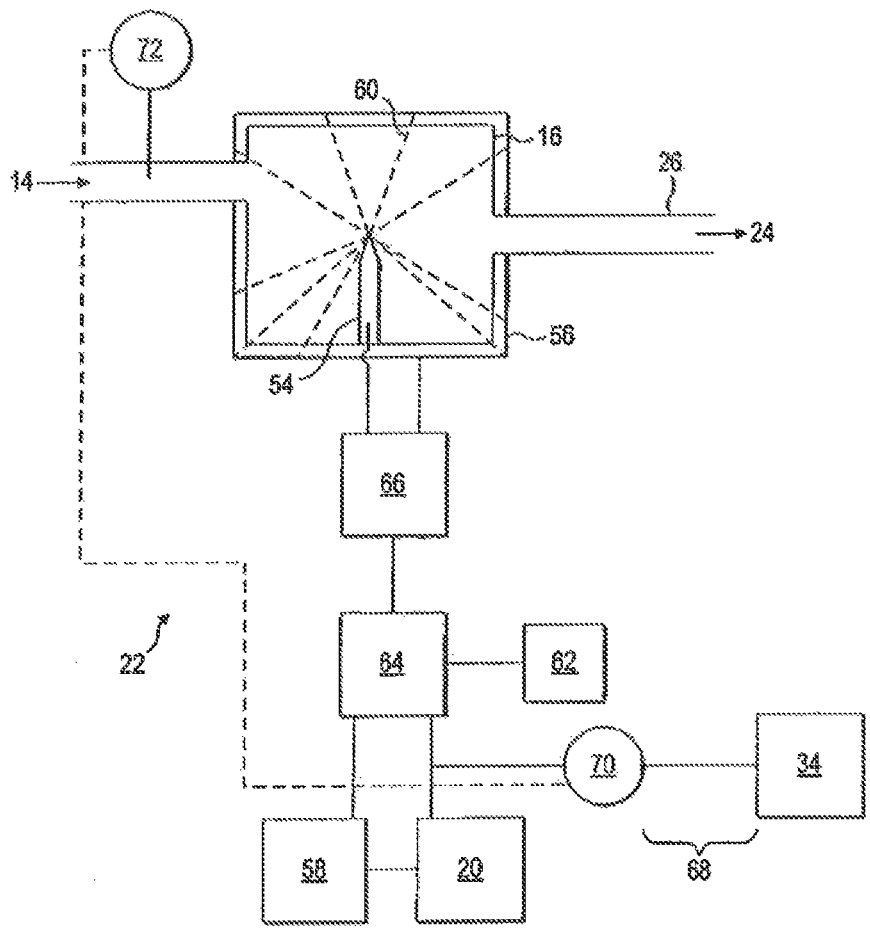
FIG. 4 shows schematically a plasma generator and means for energising gas in the generator.

Referring to FIG. 4, the electrodes 54, 56 are spaced apart one from another in order to generate an electric field shown by field lines 60 in substantially all of the plasma chamber 16. In this way, it is possible to increase the formation of plasma since gas in all portions of the plasma chamber interacts with the electric field.

One of the electrodes 56 is formed around a periphery of the plasma generator If the plasma generator is formed from a dielectric the electrode may be embedded in the structure of the wall of the plasma generator or on the outer surface of the wall. If the plasma generator is formed from an electrical conductor, the wall of the plasma generator itself may act as an electrode.

It has been found that plasma generation is promoted if one of the electrodes 54 is formed by a probe extending into the plasma generator. The probe is tapered at an end portion thereof to form a point for increasing the generation of plasma in the plasma generator. In this regard, the density of electric field is increased particularly in the region of the plasma generator proximate the point of the probe. The probe may be electrically insulated along its length with a dielectric.

The plasma energising means may 22 may operate in any of one or more plasma energising modes for example AC, or pulsed DC, and can be capacitively coupled or inductively coupled to the plasma chamber. In one example, signal generator 58 is configured to generate a pulsed DC output at 41 eV and 8 khz for driving the electrodes 54, 45. The pulses may be provided for the electrodes for 10 to 20% or less than 10% of the duty cycle. A low duty cycle helps to preserve electrical energy in the device whilst not significantly affecting the formation of a plasma, since when the output is low plasma continues to be generated by the cascade of charged particles in the chamber. Alternatively, a timing circuit 62 may switch the signal output off and on over required duty cycle.

In another arrangement, signal generator 58 is configured to generate an AC signal output at 1 kV and 30 to 80 kHz for driving the electrodes 54, 56. This range is greater than 20 kHz so that signal generator is not typically audible to people during use. Use at less than 20 kHz may produce audible hissing.

In the AC example shown, the plasma energising means 22 comprises an amplifier 64 for amplifying the output from the signal generator for driving the electrodes. A suitable matching circuit 66 may be provided for matching impedance of the load and the source.

A control 68 is operably connected to the plasma energising means 22 for controlling energisation of the electrodes. In this example the control 68 comprises an electrical switch 70 which when closed allows energisation of the electrodes 54, 56. The switch 70 is manually operable by a user using the previously referenced button switch 34 (which also activates valve 32). Alternatively, a separate user input device may be used to operate switch 70. The use of the same user input device for controlling the flow of gas into the plasma chamber and the energisation of the electrodes 54, 56 is desirable because preferably gas flow and energisation of the electrodes occurs at the same time or there may be a predetermined time delay between gas flow and energisation. Further, it is preferable that energisation of the electrodes does not occur unless gas flow exceeds a predetermined minimum required flow. Accordingly, the control 68 and control 30 may be integrated and comprise flow valve 32 for allowing the flow of gas 14 and switch 70 for allowing energisation of the electrodes.

As shown in FIG. 4, a sensor 72 is provided for sensing the flow of gas 14 released from the pressure vessel 12. The control 68 allows energisation of the electrodes only if the flow of gas is above a predetermined mass or volume flow rate.

Figure 5:
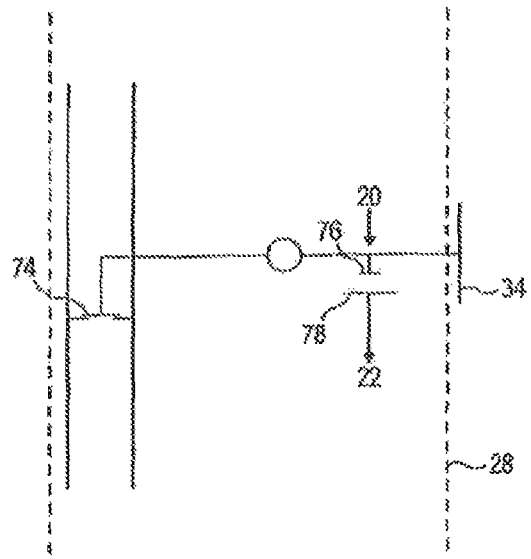
FIGS. 5 and 6 show a simplified mechanical linkage for operating the device.
Figure 6:
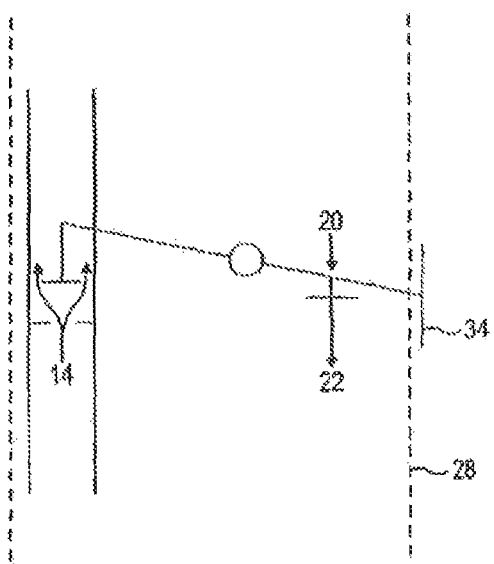

In one arrangement shown in FIGS. 5 and 6, the integrated control 30, 68 may comprise a mechanical linkage, such that operation of user input device 34 causes movement of a valve plate in valve 32 and connection of electrical contacts in switch 70. In more detail, the input device, or slide switch 34, is connected by a pivot arm to valve plate 74 and to electrical contact 76. In the condition of the mechanical linkage shown in FIG. 5, the valve plate 74 seals against a valve seat 78 closing gas flow. The electrical contact 76 is spaced from second electrical contact 80. In the condition shown in FIG. 6, the valve plate 74 is spaced from valve seat 78 opening gas flow and electrical contact between contact 76 and contact 80 is closed allowing the source of electrical energy 20 to energise the plasma generation means 22.

The source 20 of electrical energy may be one or more batteries and preferably the batteries are rechargeable. In this case, the housing 28 may comprise an electrical socket for receiving a plug connected to a mains power source and a recharging circuit 82 for recharging the batteries. Alternatively, the device comprises means for example primary windings in a recharging unit and secondary windings in the device connected to the batteries for inductively coupling the batteries to a recharging unit for recharging.

The housing 28 comprises an enclosure 84 for locating the batteries in the housing and electrical terminals (not shown) which connect to the batteries when they are located in the enclosure for supplying energy to the plasma energising means 22.

In order to permit a free range of movement of the device by a user, it is preferable that the source of electrical energy is not connected to a mains or other supply during use. It will also be appreciated that as the device may be used in a wet environment for instance a bathroom it is advantageous to avoid cabling. Further, some bathrooms do not have an electrical socket. However, the device 10 may be connected by an electrical cable to a socket during use. In this case, the source 20 of electrical energy may comprise a transformer and the housing comprises a socket for receiving a plug connected to an electrical power supply. The transformer is adapted to supply energy in a form suitable for the plasma energising means 22. The plug and transformer may be adapted for connection to the energy supply of a vehicle, for example by inserting the plug into a socket of a cigarette lighter of the vehicle and delivering suitable power to the plasma energising means.

The applicator 18 may take any suitable form for directing gaseous plasma from the plasma generator 16 to a treatment region. In its simplest form the applicator may comprise an opening in the plasma chamber. However, as shown in FIG. 1, the applicator 18 comprises an opening 26 for forming the plasma plume 24 and a duct 88 for ducting a resulting afterglow from the plasma generator 18 to the head. The duct is preferably around 1 mm to 5 mm in diameter which is sufficiently small to cause a rapid through flow of plasma to the treatment region. The duct can be straight as shown and configured so as to allow access to a treatment region. The applicator has a length which is typically less than about 10 cm.

The head may take the form of an opening or alternatively may comprise a nozzle for concentrating flow. The head is spaced from the plasma generator sufficient to protect a user from the high voltages used to generate the plasma and reduce the risk of contamination of the plasma chamber.

In three examples as shown in FIGS. 7 to 9, the device 10 is adapted to treat an oral region of a human or animal body and the applicator head is configured to generate a flow of reactive species suitable for such oral treatment.

Referring first to FIG. 8, the applicator 90 comprises an applicator head 92, a central portion 94 having one or more ducts for ducting a gas in which there is an afterglow to the head and also for ducting the gas away from a treatment region, and a connecting portion 96 for connecting the applicator to the housing 28. Head 92 forms a cavity which is sized and shaped, and formed from flexible material to receive a treatment region for example two teeth. The cavity can alternatively be shaped to receive only one tooth or more than two teeth. The head 92 is adapted such that when the cavity receives the teeth substantially all of the surface area of the enamel of the teeth, and optionally a proximate portion of gingiva, is exposed to plasma or other active gas species for treatment.

The connecting portion 94 is configured to engage with a complementary connecting portion 96 at an end of the housing 28 for fixing the applicator to the housing. The applicator connecting portion 94 comprises a plurality of formations, or keys, 95 which are received in a respective plurality of recesses, or key holes, 97 in the housing connecting portion 96. Once received in the recesses, the applicator and housing are relatively rotated to lock the applicator in place.

The connecting portions 94, 96 are configured to allow activation of one or more functions of the device 10 when connected and to prevent activation of functions when not connected. Similarly, the connection of one applicator to the housing may allow activation of one set of functions whilst the connection of another applicator to the housing may activate another set of functions. The connection of applicator 90 to housing 28 is configured to allow activation of the plasma energising means 22 and of gas flow to plasma chamber 16 when user input device 34 is operated. Without such connection, operation of the user input device cannot activate these functions.

Figure 10:
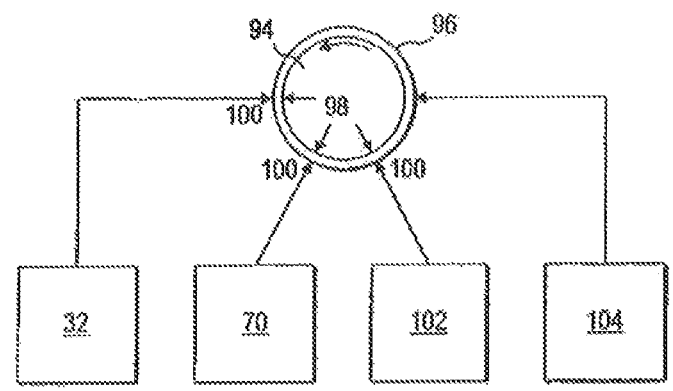
FIG. 10 shows schematically connection of the applicator shown in FIG. 8 to the housing.

As shown in FIG. 10, the connecting portions 94, 96 may comprise complementary electrical contacts which are closed to allow activation of certain, selected, functions, The arrangement is shown schematically in FIG. 10. In FIG. 10, connecting portion 94 is rotatable in connecting portion 96 to lock the applicator to the housing. When locked, electrical contacts 98 on the connecting portion 94 contact electrical contacts 100 on the connecting portion 96 thereby closing respective electronic switches allowing activation of the gas flow by valve 32, activation of the plasma energising means by switch 70, and activation of evacuation means 102 (described below). Activation of means 104 for imparting motion to a tooth brush head is not allowed in this arrangement.

Figure 11:
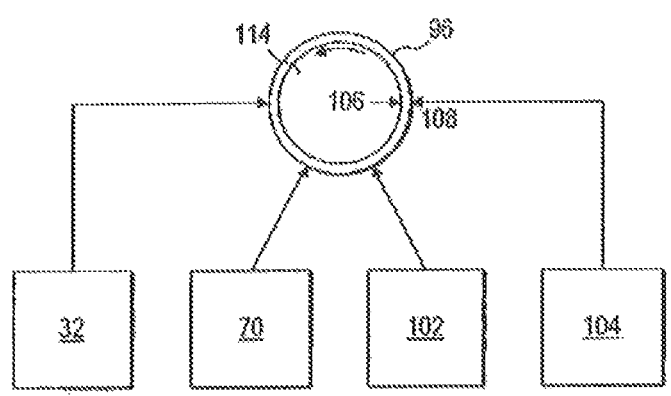
FIG. 11 shows schematically connection of the applicator shown in FIG. 7 to the housing.

When a different applicator is connected to the housing different functions of the device are allowed. In this regard, FIG. 11 shows schematically an applicator 110 illustrated in more detail in FIG. 7. Applicator 110 comprises an applicator head 112 similar to a typical tooth brush comprising bristles for cleaning teeth. Applicator 110 further comprises connecting portion 114 for engaging with connecting portion 96 of the housing 28. Ducting is not required in applicator 110 between the connecting portion 114 and the head 112 as the applicator 110 is designed to be used without plasma treatment. As shown in FIG. 11, when connection portion 114 is received in connecting portion 96 and rotated to lock applicator 110 to the housing 28, electrical contact 106 on connecting portion 114 contacts electrical contact 108 on the connecting portion 96 thereby closing an electronic switch allowing activation of means 104 for imparting motion to a tooth brush head, or other means for aiding teeth brushing. The other functions of device 10 (32, 70, 102) are deactivated in this arrangement so that plasma is not delivered when normal teeth brushing is performed.

Although applicator 110 is shown comprising an electrical contact for activating vibration for aiding teeth brushing, instead connecting portion 114 may be devoid of electrical contacts and the applicator 110 is then used as a normal tooth brush. If provided, vibration means 104 may comprise an electric motor for driving a drive shaft having an eccentric shaft portion connected to the applicator for vibrating, or otherwise moving, the applicator head 112. Alternatively, the motor is adapted to rotate the head to aid teeth cleaning.

Referring again to FIG. 8, applicator 90, which is also shown in FIG. 2, comprises in central portion 94 a duct 88 for ducting gas in which there is an afterglow from the plasma chamber to the applicator head 92 and ducts 116 for ducting plasma or gas away from the treatment region. Ducts 116 form an exhaust duct in the applicator 90 extending from the treatment region and in fluid communication with pumping means 118. The pumping means 118 is driven by a motor 120 for pumping gas or plasma from the treatment region. The evacuation means 102 including components 116, 118, 120 evacuates gas or plasma from the treatment region after treatment so that, particularly in oral treatment, a user does not inhale significant quantities of gas or plasma.

The exhaust gas exhausted by the evacuation means 102 may be used to cool the parts of the device susceptible to over-heating, The exhausted gas may be filtered by an activated filter 119 e.g. rubber, silica, charcoal, zeolite.

Alternatively, a separate pumping means may be supplied to pump cool air over the internal components of the device. Still further of source of fluid such as carbon dioxide or water may be provided which can be released to cool the components. The internal components of the device 10 susceptible to heating may be provided with heat dissipation means such as fins or in a separate arrangement the device could be designed to measure the electrical input and mass of gas input. Thus heat transfer could be measured and a safety feedback system designed.

A control is provided for controlling operation of the evacuation means. The control is preferably integrated with controls 30, 68 and comprises an electronic switch for activating the motor 120 operably connected to the user input device 34. Accordingly, the control is operable to control the evacuation means to evacuate gas or plasma from the treatment region when gas is supplied to the plasma chamber and the plasma energising means generates the plasma. In order to increase the efficiency of evacuation of plasma or gas from the treatment region, the evacuation means 102 is configured to cause a flow of gas or plasma away from the treatment region which is greater than the flow of gas caused by release from the gas capsule 12 and into the treatment region.

A third applicator 122 is shown in FIG. 9 which is generally similar to applicator 90 shown in FIG. 8 although with a different head and without the evacuation ducts 116. Applicator 122 comprises an applicator head 124 which comprises a plurality of fine hollow tubes 125 for directing plasma or active gas species onto a treatment region such as the teeth of a user. The fine hollow tubes may be formed by any suitable technique, such as extruding. The tubes are connected to a manifold cavity 127 in the head for distributing generally equally plasma or active species to the tubes.

Figure 12:
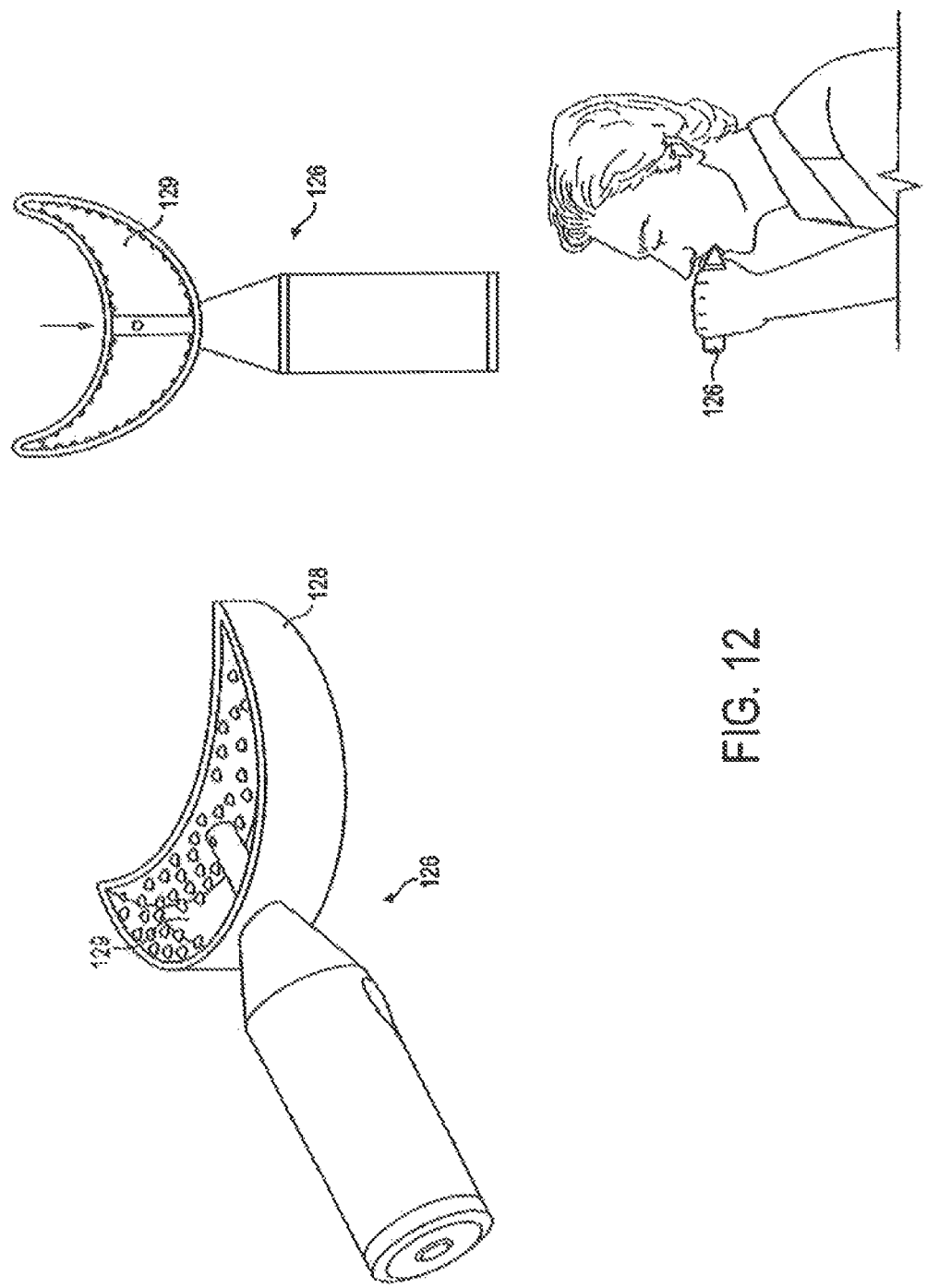
FIG. 12 shows a fourth applicator of the device.

FIG. 12 shows a fourth applicator 126. Applicator head 128 is similar in shape to a gum shield as used in sports and comprises one or more channels 129 configured to be located in the mouth of a human or animal body for directing the flow plasma or active species for treating a plurality of teeth. In more detail each channel is generally arch shaped to correspond with the teeth on the upper or lower mandible. Alternatively, the applicator head may comprise two such channels one for directing upwardly and one for directing downwardly for treating both the upper and lower sets of teeth simultaneously.

The device 10 may comprise a single applicator for example the applicator 90 shown in FIG. 8 or alternatively the device 10 may comprise a plurality of interchangeable applicators as shown in FIGS. 7 to 9 and 12, each for performing a specific function. For example, it is desirable to enable a user to brush teeth in the normal way using the device 10 with applicator 110, optionally with vibration, and also to be able to treat the teeth with plasma or other active species with any one or more of applicators 90, 122, 126.

Referring to FIG. 1, the device 10 may comprise a display 130 for displaying a value representative of a condition of the device, for example, one or more of the gas content of the gas capsule 12, the amount of charge remaining in the source of electrical energy 20, or a temperature of the plasma plume emitted from the applicator. The display may be a graphical LCD. Additionally or alternatively, means 132 may be provided for alerting a user when a condition of the device, such as gas content of the pressure vessel, charge in the source of electrical energy, or temperature of the plasma plume decreases or increases beyond a predetermined amount. The alerting means 132 may comprise means for generating a sound which is audible to user or a warning light, such as an LED, prompting the user to recharge or replace the gas capsule or the source or to remove the device from the treatment region to avoid harm.

The gas capsule 12 preferably contains a gas or mixture of gases, such as Helium, or other noble gases for forming a non-thermal gaseous plasma in the plasma generator. That is, the gas can form a plasma when relatively low amounts of energy are input to the plasma generator 16 by the plasma energising means 22, In the formation of a gas plasma, the generated electric field causes high energy electrons to strike the gas atoms or molecules removing an electron thereby forming a sea of electrons and ions. In general, the generation of a non-thermal plasma flow or plume at temperatures less than about 40° C. can be achieved in a gas based on helium. Alternatively, the gaseous plasma may be based on one or more other noble gases. Relatively low temperatures are required when treating the human or animal body because high temperatures can kill biological cells causing necrosis or pain.

Figure 13:
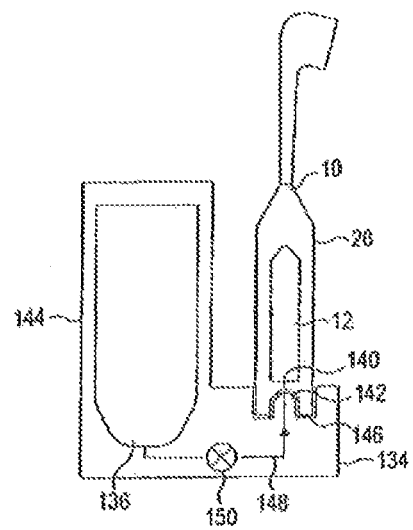
FIG. 13 shows the device seated in the charging unit from one side.
Figure 14:
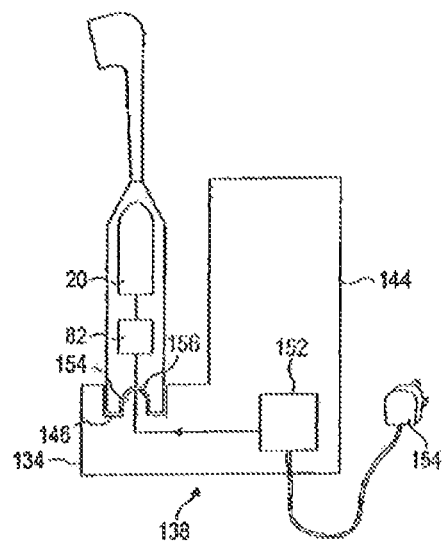
FIG. 14 shows the device seated in the charging unit from the other side.
Figure 15:
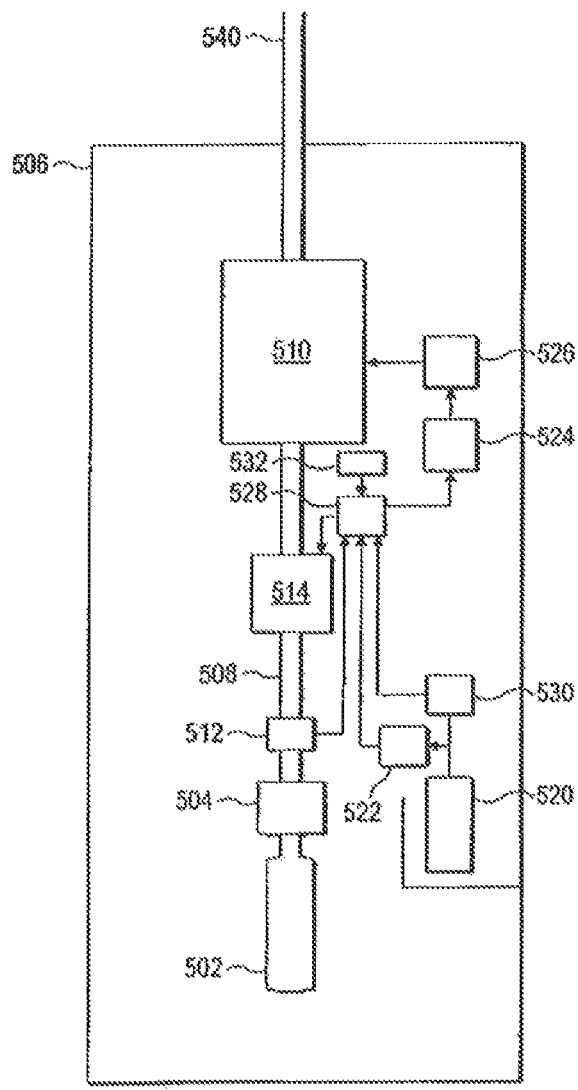
FIG. 15 is a schematic diagram illustrating means for providing electrical plasma generating energy to the plasma generator of a device according to the present invention.

Referring to FIGS. 1, 13 and 14, apparatus is shown comprising device 10 and a recharging unit 134. The recharging unit comprises a recharging pressure vessel 136 containing gas for supplying gas to the gas capsule 12 of the device 10; and electrical recharging means 138 for recharging the source of electrical energy 20 in the device. In an alternative arrangement the recharging unit may comprise only one of the recharging pressure vessel 136 and the electrical recharging means 138. Replacement pressure vessels 12 may be used when a previous vessel is depleted of gas by use in the device, or fresh batteries are used to replace the source 20 when discharged.

The recharging unit and device gas capsule 12 comprise respective recharging valves 140, 142 which can be opened when the gas capsule are connected as shown to allow the supply of gas to the device gas capsule 12 and are closed when the pressure vessels are not connected. The valve arrangement may be similar to the arrangement shown in FIG. 3.

The recharging unit 134 consists of a stand having upright portion 144 for storing the recharging pressure vessel 136. The recharging pressure vessel is relatively larger and may have a larger volume of pressure and can contain sufficient gas to refill the device a multiplicity of times, perhaps as much as twenty times. The recharging unit also comprises a seat 146 for seating the device. When the device 10 is seated in the recharging unit the pressure vessels 12, 136 are connected to allow the supply of gas to the device gas capsule 12. In this regard, a conduit 148, optionally including a valve 150, is provided having a first end portion adapted for engaging with and opening the recharging valve 140 of the device gas capsule 12 and a second end portion connected to the recharging pressure vessel 136. Accordingly, when the device 10 is seated in the recharging unit 134, the pressure vessel 12 of the device 10 is automatically refilled.

In an alternative arrangement, rather than seating the whole of the device 10 on the recharging unit for recharging, the seat 146 seats a device gas capsule 12 when it has been removed from the device. Accordingly, when the device gas capsule 12 is seated in the recharging unit the pressure vessels 12, 136 are connected to allow the supply of gas to the device gas capsule.

In this case, the apparatus may comprise at least two device gas capsule 12. At any one time one or more device gas capsule 12 can be seated in the recharging unit 134 for recharging and one device gas capsule 12 can be housed in the device housing 28 for use in generating a gas flow.

As shown in FIG. 14, the electrical recharging means 138 comprises a control circuit 152 for receiving electrical energy from, for instance, a mains supply through a plug 154 and supplying the electrical energy for recharging the source of electrical energy 20 in the device 10 when the source of energy 20 is connected to the electrical recharging means 138. When the device is seated in the recharging unit in seat 146 the source of energy 20 is automatically connected to the electrical recharging means if the recharging unit is connected to the mains supply.

One of the seat 146 and the device 10 may include a formation, or protrusion, 154 and the other includes a recess 156 for mating for example for allowing close proximity of primary and secondary coils of an inductively coupled charging means for charging the source 20.

In an alternative arrangement, the source 20 may be recharged by removing it from the device 10 placing it on the seat 146 so that it is connected to the recharging unit and recharging it with the recharging means 138.

In use of the device 10 for example for whitening, cleaning, sterilising or healing an oral region of a body, a user selects an appropriate applicator 18 for fixing to the housing 28. Depending on the applicator, selected functions of the device 10 can be activated when the user operates the user input device 34. For plasma treatment, the operation of the user input device opens valve 32, doses switch 70 and activates the evacuation means 102. Provided there is sufficient gas flow (e.g. helium) into the plasma generator 16, the plasma energising means 22 energises gas in the plasma generator to form a plasma. Although substantially all of the plasma generator is exposed to an electric field, the degree of ionisation of the resulting plasma may be limited. A plasma flows from the generator and becomes an afterglow that flows through the applicator 18. The user positions the applicator head so that a resulting gaseous plume flows over the treatment region, for instance one or more teeth, During treatment, the evacuation means evacuates gas from the treatment region. When treatment is completed, the user operates the user input device 34 to deactivate gas flow, the plasma energising means 22 and the evacuation means 102.

Inevitably, some plume interacts with ambient air (e.g. oxygen, nitrogen and argon) causing some chemical breakdown forming active gaseous species, particularly reactive oxygen species (ROS) and reactive nitrogen species (RNS). For example, the interaction of the plume with oxygen may form hydroxyl radicals and/or ozone. Both are strong oxidants and can contribute to the beneficial, or therapeutic, effect on the treatment region as is the case with other active gaseous species.

In another embodiment, a device is configured to generate ozone or other active gaseous species without the generation of a non-thermal plasma or by using other energising techniques.

Such a device generates a flow of a non-thermal gaseous species and has equivalent features to device 10 except where otherwise stated. The device comprises a gas capsule for holding a gas under pressure and forming a flow of gas through a reaction chamber to an applicator when released from the vessel. Gas released from the gas capsule is ionised in the plasma generator to form an active gaseous species.

The device further comprises a source of electrical energy and energising means electrically connected to the source of electrical energy for energising gas in the plasma generator to form the gaseous species.

An applicator directs the flow of gaseous species from the plasma generator for generating a flow of gaseous species from the device. A housing houses the gas capsule, plasma generator, source of electrical energy, and energising means. The housing is sized and of a weight such that the device can be held and operated by a user by hand and the flow of gaseous species directed to treat a treatment region of an object or human or animal body. The gas capsule may contain oxygen and in this case the excited gaseous species formed is singlet oxygen. Ozone is formed by reaction of oxygen molecules with the singlet oxygen. Referring now to FIG. 1, there is shown schematically a form of the device according to the invention in which a 12V DC signal is converted to a 6 kV AC signal for operating the plasma generator on a 15% duty cycle. A low duty cycle helps to preserve electrical energy in the device whilst not significantly affecting the formation of a plasma.

The device shown in FIG. 5 has a cylindrical gas capsule 502 of water capacity up to 100 ml. but is preferably in the order of 20 ml. The gas capsule 502 is fitted with an on-off valve 504. The valve 504 may be of the same kind as described herein with reference to and as shown in FIG. 3. The valve 504 may be actuated by an arrangement similar to that described with reference to and as shown in FIG. 3. To prepare the device for operation, the gas capsule 502 is docked within a housing 506 which contains valves for controlling the supply of gas from the capsule to a generator of non-thermal gaseous plasma, the generator also being provided within the housing 506. In addition, the housing holds one or more electrical batteries for supplying a DC current and electrical means for transforming the DC voltage to an AC voltage and for applying the AC voltage to the electrodes of the plasma generator.

The housing 56 has a gas passage 508 for flow of gas from the gas capsule 502 to a plasma generator 510. The passage 508 houses, in sequence, a pressure regulator 512, a flow sensor 514, and a solenoid valve 516, all upstream of the plasma generator 510.

The housing 506 holds a 12V battery 520. The battery is provided with a display LED 522. The display LED can indicate the status of the battery, i.e. it informs the user when the available power in the battery 520 is low. The battery 520 provides power to a low voltage signal generator 524 in combination with a high voltage generator 526. A control 528, in the form of a logic circuit, is configured to receive a plurality of inputs dependent on a condition of the apparatus for selectively supplying an output to the signal generators 524 and 526. A first input comes from a main on-off switch 530. If this witch is in its "off" position neither the gas supply nor the power supply to the plasma generator is able to be initiated. A second input may be from the LED 522. If the battery is low neither the gas supply nor the power supply to the plasma generator is able to be initiated. A third input to the control is from the flow sensor 514. If the flow sensor does not detect the flow of gas to the plasma generator 510, the power supply to the plasma generator 510 is not able to be initiated. Desirably, the logic circuit 528 includes time delay means which delays generation of a power output to the plasma generator 510 for a predetermined time after the flow sensor 514 senses the passage of gas to the plasma generator. This enables the gas to purge the plasma generator 510 prior to the initiation of plasma generation.

The device shown in FIG. 5 is provided with a secondary on-off switch 532. When the switch 532 is in its "off" position the solenoid valve 516 is in its closed position. Gas is therefore prevented from flowing to the plasma generator 510. On the other hand, when the switch is in its "on" position, the logic circuit sends a signal to the solenoid valve 516 so as to open it, provided the main switch 530 is also in its "on" position. The flow of gas to the plasma generator is therefore detected and a plasma generating signal is able to be sent to the plasma generator 510.

If desired, a single on-off switch may perform the functions of both the switches 530 and 532.

The plasma generator 510 has an outlet communicating with an applicator 540 configured to direct a plume of non-thermal reactive gaseous species at a target surface.

The signal generators 524 and 526 may through a number of components and circuits (not individually shown) convert the electrical current from a 12V battery into a pulsed output voltage in the range 4 to 6 kV at a frequency of 2-10 kHz which is suitable for generation of a non-thermal plasma. Such circuits and components are well known in the fields of electronics and electrical engineering and need not be described in full detail herein. Essentially circuits of a kind used with xenon flashlamps can be used to enable the battery to charge a capacitor up to, say, 320V. A transformer can be used to set up the voltage and enable voltage pulses in the desired range of 4 to 6 kV to be generated. In order to produce clear, well defined pulses it is desirable to keep the number of turns and inductance of the windings of the transformer to low levels and to have modest step-up ratios. This approach helps keep the unwanted parasitic elements of leakage inductance and stray winding capacitance to a minimum, both of which contribute to pulse distortion.

Because a pulse transformer has a low primary winding inductance, the magnetising current that generates the working magnetic flux in the core is substantial; leading to significant stored magnetic energy in the transformer during the pulse generation. For an efficient design, this magnetic energy is recovered at the end of the pulse and temporarily held in another form (usually as a charge on a capacitor) ready to generate the next pulse.

In any case, the magnetic flux in the core is to be returned to zero before the next pulse is generated otherwise the flux builds up with successive pulses until the core saturates, at which point the transformer stops working and acts as a short circuit to the drive electronics.

A common method of magnetic energy recovery in switched-mode power supply transformers, which may be used in this case, is through the use of a so-called "flyback" winding. This is usually identical to the primary winding and both wound on the core at the same time (a bipolar winding) in order to ensure a high level of magnetic coupling between the two. The flyback winding connects between ground and the reservoir capacitor of the DC supply via a blocking diode, During pulse generation a fixed voltage is applied to the primary winding and current ramps up building up magnetic flux in the core—this induces an equal and opposite voltage across the flyback winding (but no current flows due to the blocking diode). Interruption of the primary current at the end of the pulse forces the magnetic field to start collapsing which reverses the induced voltage across the flyback winding and causes current to flow back into the supply capacitor. The flux and current ramp down smoothly to zero ready for the next pulse.

Another suitable transformer configuration is a push-pull design in which two identical bifilar wound primary windings are alternatively connected to the DC power supply. The phasing of the windings is such that magnetic flux in the core is generated with opposing directions which each is alternately driven.

A push-pull design also allow stored magnetic energy to be recovered and returned to the supply capacitor in a very similar fashion to the flyback approach, where the blocking diode now becomes an active transistor switch. The same transformer design may now be used for either approach.

Although the push-pull design requires additional switching transistor and control, it allows the possibility of doubling the change in magnetic flux within the limits of the core by using both positive and negative flux excursions. The flyback design outlined above only allows unipolar flux excursions.

The invention claimed is:

1. A self-contained, hand held, hand operated device for generating a flow of a non-thermal gaseous species, comprising:
   a housing having a length of 30 cm or less, and a breadth of 5 cm or less, the housing containing;
      a gas capsule holding a gas under pressure wherein the gas may be released from the capsule;
      a reaction generator for receiving gas released from the capsule and for generating the gaseous species;
      a conduit connecting the gas capsule to the reaction generator;
      a source of electrical energy; and
      energizing means electrically connected to the source of electrical energy for generating the gaseous species in the reaction generator;
   a control for selectively releasing gas from the gas capsule, wherein the control is operably connected to the energizing means for controlling activation thereof; and
   a sensor for sensing the flow of gas released from the gas capsule, wherein the control allows activation of the energizing means only if the flow of gas is above a predetermined mass or volume flow rate.

2. A device as claimed in claim 1, further comprising an orifice plate and an expansion chamber wherein the gas released from the gas capsule passes through the orifice plate to the expansion chamber for controlled release to the reaction generator.

3. A device as claimed in claim 1, further comprising a flow regulator for regulating the flow of gas between the gas capsule and the reaction generator.

4. A device as claimed in claim 1, wherein the energizing means comprises at least one electrode for generating an electric field in the reaction generator and a signal generator for generating an electrical signal for driving the at least one electrode.

5. A device as claimed in claim 4, wherein the signal generator generates a pulsed DC or an AC signal.

6. A device as claimed in claim 4, wherein said signal generator is configured to generate a low duty cycle signal in which the energy is provided to the at least one electrode for less than 10% of the duty cycle.

7. A device as claimed in claim 4, wherein the at least one electrode is insulated from gas in the reaction generator by a dielectric to reduce arcing.

8. A device as claimed in claim 4, wherein the energizing means comprises two electrodes and the reaction generator is a plasma generator, one electrode is formed around a periphery of the plasma generator and the other electrode is a probe extending into the plasma generator.

9. A device as claimed in claim 1, wherein the device is for whitening or cleaning teeth of a human or animal.

10. A device as claimed in claim 1, wherein the gaseous species is a non-thermal gaseous plasma.

11. A device as claimed in claim 10, wherein the non-thermal gaseous plasma has a temperature of less than 40° C.

12. A device as claimed in claim 1, further comprising an applicator connected to the housing for conveying the gaseous species from the reaction chamber and applying the gaseous species to the treatment region.

13. A device as claimed in claim 12, wherein the applicator has an end configured for insertion into the oral cavity of a person using the device.

14. A device as claimed in claim 1, further comprising
   a recharging pressure vessel containing gas for supplying gas to the gas capsule; and
   an electrical recharging means for recharging the source of electrical energy.

15. A device as claimed in claim 1, wherein the gas capsule has an internal volume in the range of 10 ml to 100 ml.

16. A device as claimed in claim 1, wherein the gas capsule contains gas stored at a pressure of at least 60 bar.

17. A device as claimed in claim 1, wherein the source of electrical energy is one or more rechargeable batteries.

* * * * *